United States Patent [19]

Edwards et al.

[11] Patent Number: 5,456,811
[45] Date of Patent: Oct. 10, 1995

[54] METHOD AND APPARATUS FOR MEASURING SILVER ION ACTIVITY

[75] Inventors: Stephen J. Edwards, Pinner, United Kingdom; James R. Sandifer, Rochester, N.Y.

[73] Assignee: Eastman Kodak Company, Rochester, N.Y.

[21] Appl. No.: 289,075

[22] Filed: Aug. 11, 1994

[30] Foreign Application Priority Data

Sep. 9, 1993 [GB] United Kingdom ............... 93018677

[51] Int. Cl.⁶ ................................................. G01N 27/26
[52] U.S. Cl. ......................... 204/153.13; 204/153.1; 204/402; 204/416; 204/419; 204/412; 204/435
[58] Field of Search ............................... 204/402, 416, 204/419, 435, 412, 153.13, 153.1

[56] References Cited

U.S. PATENT DOCUMENTS

| | | | |
|---|---|---|---|
| 3,458,421 | 7/1969 | Dahms | 204/402 |
| 3,523,883 | 8/1970 | Waclawik et al. | 204/402 |
| 4,201,647 | 5/1980 | Spaziante et al. | 429/91 |
| 4,601,792 | 7/1986 | Tenygl | 204/413 |
| 5,217,112 | 6/1993 | Almon | 204/153.1 |
| 5,298,129 | 3/1994 | Eliash | 204/412 |
| 5,324,400 | 6/1994 | Eliash et al. | 204/412 |

FOREIGN PATENT DOCUMENTS

WO92/06368  4/1992  WIPO.

OTHER PUBLICATIONS

Patent Abstracts of Japan, vol. 015, No. 166, p. 1195, Apr. 25, 1991 (JP 03031753).
Derwent Publications Ltd., (91–084704) No Month or Year Available.
Patent Abstracts of Japan, vol. 010, No. 369, p. 525, Dec. 10, 1986 (JP 61162744).
Derwent Publications Ltd., (86–234644) No Month or Year Available.
Patent Abstracts of Japan, vol. 010, No. 072, p. 438, Mar. 22, 1986 (JP 60211354).

*Primary Examiner*—John Niebling
*Assistant Examiner*—Bruce F. Bell
*Attorney, Agent, or Firm*—Paul A. Leipold

[57] ABSTRACT

A method of measuring the silver ion activity of a mixed halide solution or dispersion comprises measuring the potential difference between a silver halide coated silver electrode and a reference electrode immersed in the solution or dispersion. Prior to measuring the potential difference an electrical pulse is applied to the silver electrode which in a first phase electrochemically strips the electrode surface and in a second phase electrochemically coats the electrode with a silver halide having the halide ion ratio of the solution or dispersion.

23 Claims, 2 Drawing Sheets

METHOD AND APPARATUS FOR MEASURING SILVER ION ACTIVITY

FIELD OF THE INVENTION

The invention relates to a method and apparatus for measuring the silver ion activity of halide solutions and dispersions.

BACKGROUND OF THE INVENTION

In electroanalytical measurements, a sensing electrode is used in combination with a reference electrode. When both electrodes are immersed in a solution of an ionic salt, a potential difference is established between the electrodes whose magnitude is a function of the concentration of the dissolved ionic species.

In measuring silver ion activity in a halide solution or dispersion, a bare silver electrode will respond to the silver ion activity but will respond relatively slowly to changes in halide ion activity. The response can be increased by coating the surface of the silver electrode with a layer of the silver halide. The silver ion activity at the electrode surface is, therefore, directly affected by changes in halide ion activity in accordance with the solubility product of the silver halide.

Potentiometric methods are known for measuring the equilibrium silver ion activity in mixed silver halide solutions and dispersions. Two methods have been used in process control environments where the halide ion is in excess and the silver ion activity is relatively small.

One method employs a silver electrode which has been coated with a layer of silver halide either chemically or electrochemically. This electrode will respond to the particular halide coated and hence give the silver ion activity in equilibrium with the particular halide coated. Good precision, accuracy and a fast response time are obtained in solutions or dispersions consisting of the halide ion coated. However, in solutions or dispersions of mixed silver halide, the electrode coating is chemically changed to reflect the new ratio of halide ions and takes several minutes to settle to the correct value for the equilibrium silver activity. This type of electrode is unsuitable for process control of mixed halide solutions or dispersions.

A second method uses a membrane of silver halide where the electrode contact is either directly made to the rear of the membrane or is made via a filling solution containing an electrode with a fixed potential. A membrane or pellet is prepared from either particles of a single silver halide or from a mixture containing two or more halides and possibly silver sulphide. The membrane electrode has a smaller surface area to be chemically changed and therefore responds slightly more quickly than the previously described electrode. However, due to the mixed nature of the membrane and the method of construction, the value obtained is not always theoretically predictable. For this reason, careful calibration of the membrane electrode is required. Hence, this electrode is also not recommended for use in the process control of mixed halide solutions or dispersions.

PROBLEM TO BE SOLVED BY THE INVENTION

The invention solves the problem of providing a method of measuring the silver ion activity of a mixed halide solution or dispersion with a precision and accuracy equal to or better than that of the method described above using a silver electrode coated with a silver halide coating, and with a faster response time.

SUMMARY OF THE INVENTION

The invention provides a method of measuring the silver ion activity of a mixed halide solution or dispersion which comprises measuring the potential difference between a silver halide coated silver electrode and a reference electrode immersed in the solution or dispersion characterised in that prior to measuring the potential difference an electrical pulse is applied to the silver electrode which in a first phase electrochemically strips the electrode surface and in a second phase electrochemically coats the electrode with a silver halide consistent with the halide ion ratio of the solution or dispersion.

The invention also provides apparatus for measuring the silver ion activity of a mixed halide solution or dispersion which comprises a silver halide coated silver electrode, a reference electrode and means for measuring the potential difference between the electrodes when they are immersed in a mixed halide solution or dispersion characterised in that the apparatus further comprises means for applying an electrical pulse to the silver electrode so that, when the apparatus is in use, a first phase of the pulse electrochemically strips the electrode surface and a second phase of the pulse electrochemically coats the electrode with a silver halide consistent with the halide ion ratio of the solution or dispersion.

ADVANTAGEOUS EFFECT OF THE INVENTION

The measured value changes rapidly when the ratio and kind of halide ion are changed. Response times of less than five seconds have been achieved compared to response times of 2 to 15 minutes using conventional systems.

The same electrode can be used for all solutions and dispersions containing mixed halides.

The electrode can be calibrated with only a few standard solutions. Different standard solutions are not needed for different halide solutions or dispersions.

The electrode is not irreversibly changed by mixed halide solutions or dispersions allowing the same electrode to be used for monitoring several batches of product.

DETAILED DESCRIPTION OF THE INVENTION

Figure 1:
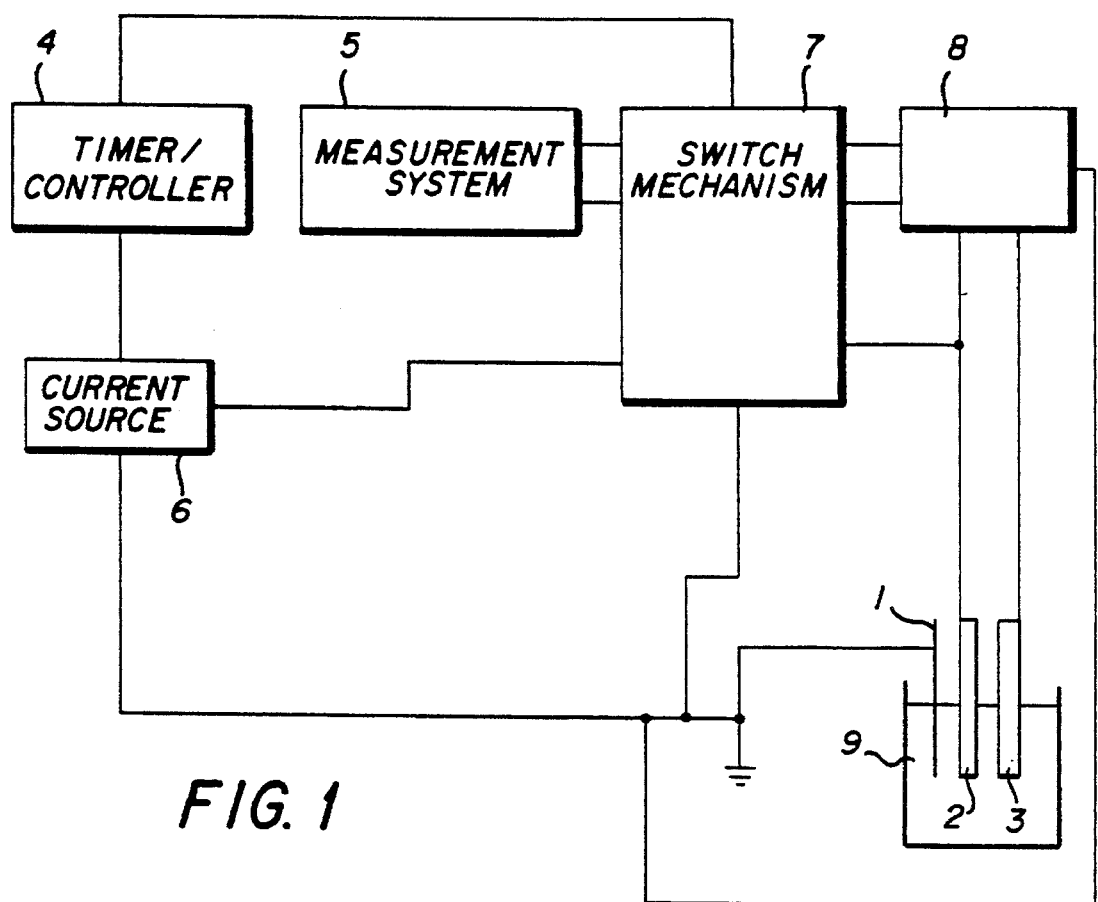
FIG. 1 is a schematic representation of apparatus in accordance with the invention.

The surface composition of the silver halide coated silver electrode is adjusted through an electrochemical conversion step. This is achieved by applying an electrical pulse to the electrode prior to measurement. The pulse is arranged so that the first phase strips the surface of a thin layer. The second phase then coats the electrode with a silver halide consistent with the halide ion ratio of the solution or dispersion. The measurement is then taken. The cycle comprising the application of the pulse and subsequent measurement is preferably repeated. A new electrode surface is produced for each cycle. The measured value is close to the theoretical value and the response to changes of halide ratio is as fast as the cycle period.

The electrical pulse comprises two phases of opposite polarity. Suitable forms of electrical pulse include wave pulses, e.g., sinusoidal and square wave pulses. Preferably, the electrical pulse is a square wave pulse wherein the amplitude and frequency of each phase may be different. Preferably, the amplitude and/or time of the first phase which strips the electrode is greater than the amplitude and/or time of the second phase which coats the electrode. In this way, complete stripping of the electrode down to silver is ensured.

The electrical pulse may provide an alternating current of from 0.01 mA to 10 mA, preferably from 0.1 mA to 1 mA. Alternatively, the electrical pulse may be a controlled voltage pulse of between −100 mV and +700 mV versus a reference electrode, e.g., a saturated calomel electrode. The value of the voltage pulse can either be preprogrammed or can be derived from the previous measurement cycle. The time period of the pulse may be from 1 msec to 1 sec, preferably from 2 msecs to 100 msecs.

The surface area of the silver halide coated silver electrode may range from 0.5 to 600, preferably from 1 $mm^2$ to 20 $mm^2$.

Preferably, the application of the pulse is followed by a period of delay before measurement occurs. Preferably, the cycle of events represented by the application of the pulse, the delay and the measurement is repeated a number of times. The cycle of events may take from 2 msecs to 10 secs, preferably from 10 msecs to 1 sec.

Silver ion activity is determined from the measurement of the potential difference between the silver electrode coated with silver halide and the reference electrode. Any conventional reference electrode may be used, e.g., a calomel electrode, a silver/silver chloride electrode, and any remote electrode using a bridge solution.

In a preferred embodiment of the apparatus of the invention, the means for applying an electrical pulse to the silver electrode comprises a counter electrode and means for generating an alternating current between the silver electrode and the counter electrode.

The counter electrode may be a metal electrode, e.g., a silver, stainless steel or platinum electrode. The counter electrode may be a metal container in which the silver halide solution or dispersion is contained.

Preferably, the apparatus further comprises switching means for alternately connecting and disconnecting the means for applying an electrical pulse and the means for measuring the potential difference.

Preferably, the apparatus further comprises timing means for controlling the duration of the pulse, the duration of measurement of the potential difference and any delay therebetween, and control means for controlling the size of the pulse.

To achieve a continuous measurement, several silver halide coated silver electrodes can be used together with the pulse and measurement steps overlapping without coinciding.

Precision and accuracy can be increased by using an array of silver halide coated silver electrodes with some computer processing yielding an average or processed value. For example, each individual value can be examined to eliminate statistically erroneous results.

The invention is further illustrated by way of example in the accompanying drawings.

FIG. 1 is a schematic representation of apparatus in accordance with the invention. Counter electrode (1), silver halide coated silver electrode (2), and reference electrode (3) are in contact with a silver halide solution (9) held in a container. Electrodes (2) and (3) are connected through a high impedance amplifier (8) and a switch mechanism (7) to a measurement system (5). Electrode (2) is separately connected through the switch mechanism (7) to a constant current source (6). The counter electrode (1) is connected to the ground of the measurement and current source circuits. Current source (6) and switch mechanism (7) are connected to a timer/controller (4), e.g., a computer which controls the duration of the electrical pulse applied from the current source (6), the duration of the delay period after the pulse has been applied, the switching from the application of the pulse to the measurement of potential difference and the duration of the period of measurement.

Figure 2:
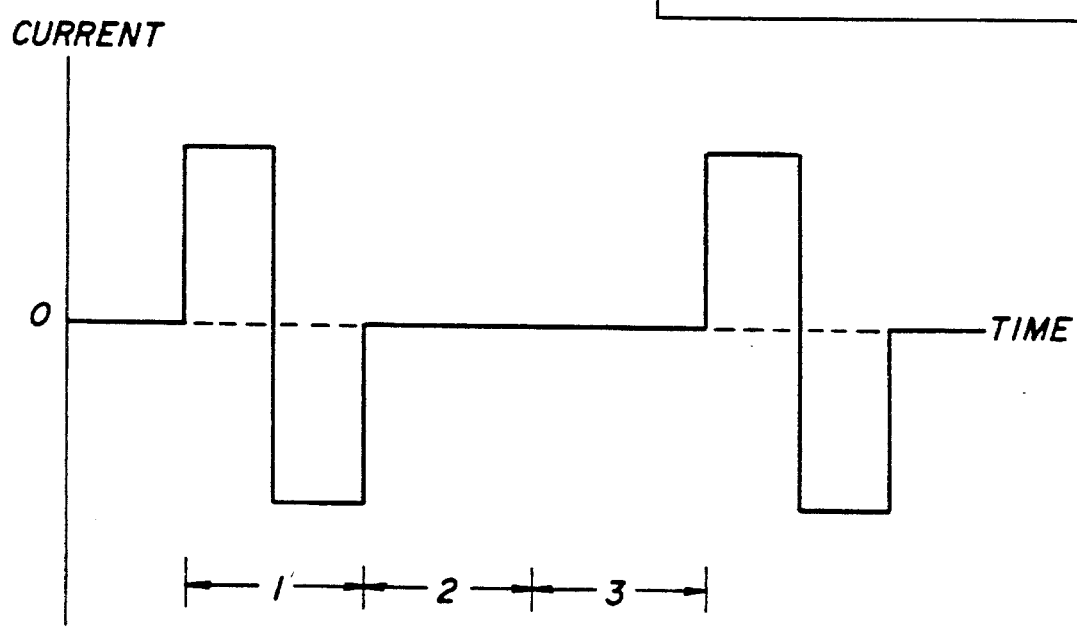
FIG. 2 is a timing diagram showing the application of an electrical pulse and subsequent measurement of silver ion activity.

FIG. 2 is a timing diagram showing the application of the electrical pulse and subsequent measurement of silver ion activity. The electrical pulse is a square wave pulse applied for the time period shown as 1 in the diagram. The square wave pulse is followed by a delay period 2 which in turn is followed by a measurement period 3. During the delay period the silver electrode is preferably grounded. The cycle of events occurring during the periods 1, 2 and 3 is then repeated.

Using the method and apparatus of the invention described above, the silver ion activity of various mixed halide solutions was measured. The silver halide coated silver electrodes had a surface area of from 10 $mm^2$ to 100 $mm^2$ with a current of from 0.1 mA to 0.5 mA being applied. The time period of the square wave pulse was from 20 msecs to 100 msecs.

The following examples illustrate the practice of this invention. They are not intended to be exhaustive of all possible variations of the invention. Parts and percentages are by weight unless otherwise indicated.

EXAMPLE 1

Using apparatus as shown in FIG. 1 above, the silver ion activity in 100 ml of $10^{-2}$M potassium bromide solution was measured. The counter electrode was a platinum electrode, the measuring electrode was a silver electrode coated with silver bromide and the reference electrode was a silver/silver chloride reference electrode.

The measuring electrode had a surface area of 10 $mm^2$ and the current applied was 0.2 mA for the first or stripping phase and 0.16 mA for the second or coating phase. In each cycle, the time period of the square wave pulse was 30 msecs, the delay period was 100 msecs and the period of measurement was 20 msecs.

Figure 3:
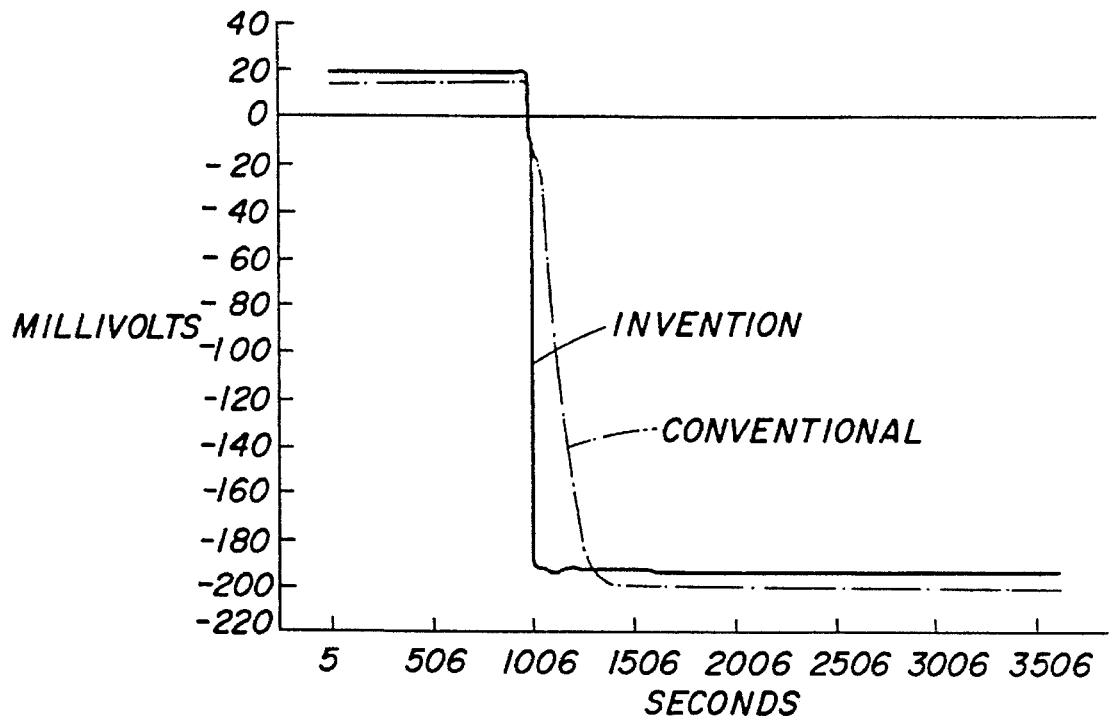
FIGS. 3 and 4 are graphical representations of the results achieved using the method of the invention compared with results achieved using a conventional method.

After approximately 14 minutes, 1 ml of 1M potassium iodide solution was added resulting in a mixed halide solution. FIG. 3 shows the response using the method and apparatus of the invention compared with the response achieved using the prior art method which relies on chemical conversion at the measuring electrode surface. It can be seen that the method and apparatus of the invention provide a significantly faster response time.

EXAMPLE 2

Using apparatus as shown in FIG. 1 above, the silver ion activity in 100 ml of $10^{-2}$M potassium chloride solution was measured. The counter electrode was a platinum electrode, the measuring electrode was a silver electrode coated with silver chloride and the reference electrode was a silver/silver chloride reference electrode.

The measuring electrode had a surface area of 10 $mm^2$ and the current applied was 0.2 mA for the first or stripping phase and 0.16 mA for the second or coating phase. In each cycle, the time period of the square wave pulse was 30 msecs, the delay period was 100 msecs and the period of measurement was 20 msecs.

Figure 4:
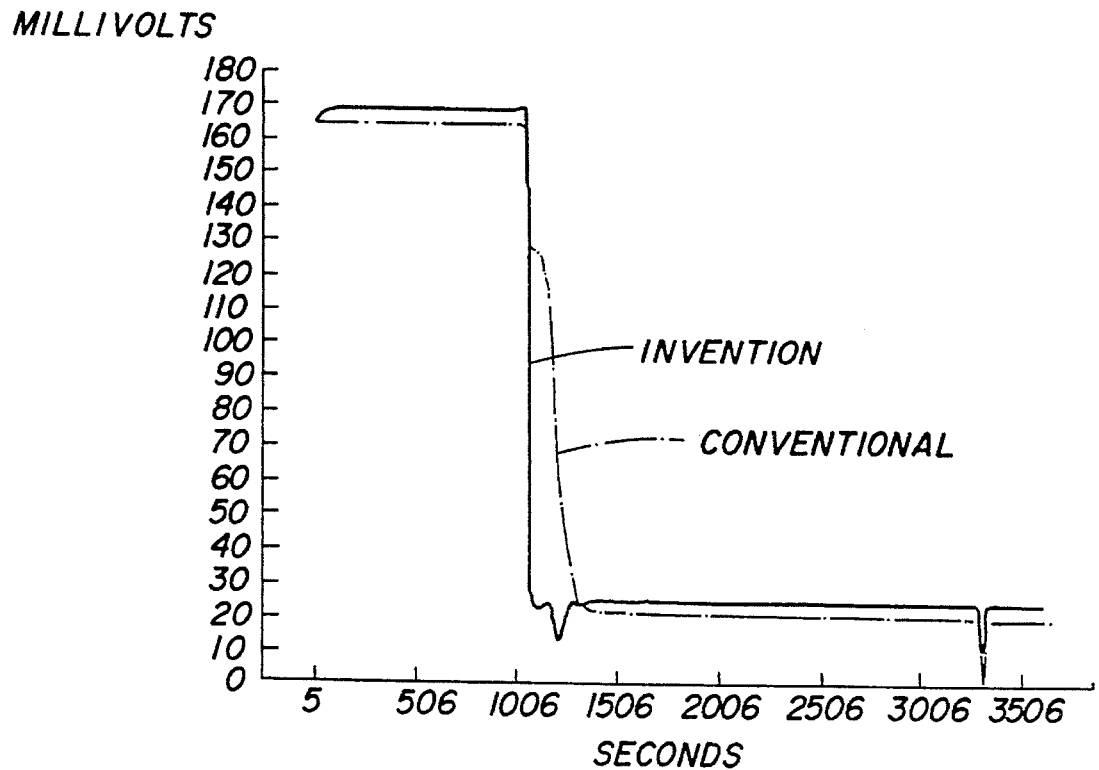

After approximately 14 minutes, 1 ml of 1M potassium bromide solution was added resulting in a mixed halide solution. FIG. 4 shows the response using the method and apparatus of the invention compared with the response achieved using the prior art method which relies on chemical conversion at the measuring electrode surface. It can be seen that the method and apparatus of the invention provide a significantly faster response time.

The invention has been described in detail with particular reference to preferred embodiments thereof, but it will be understood that variations and modifications can be effected within the spirit and scope of the invention.

We claim:

1. A method of measuring the silver ion activity of a mixed halide solution or dispersion which comprises measuring potential difference between a silver electrode and a reference electrode immersed in the solution or dispersion characterized in that prior to measuring the potential difference an electrical pulse is applied to silver electrode which in a first phase electrochemically strips the surface of said electrode and in a second phase electrochemically coats the surface of said electrode with a silver halide consistent with the halide ion ratio of the solution or dispersion and wherein the electrical pulse is a constant controlled voltage versus a reference electrode and the difference of the voltage is determined by a calculation based on a previous measurement cycle.

2. A method according to claim 1 wherein the electrical pulse is a square wave pulse.

3. A method according to claim 1 wherein the area of the surface of the silver electrode is from 1 $mm^2$ to 600 $mm^2$.

4. A method according to claim 1 wherein the application of the pulse is followed by a period of delay before measurement occurs.

5. A method according to claim 4 wherein the cycle of events represented by the application of the pulse, the second phase, and the measuring is repeated a number of times.

6. A method according to claim 5 wherein the cycle of events takes from 10 msecs to 1 sec.

7. A method according to claim 1 wherein the pulse is from 2 msecs to 100 msecs.

8. Apparatus for measuring the silver ion activity of a mixed halide solution or dispersion which comprises a silver electrode, a reference electrode and means for measuring the potential difference between the electrodes when they are immersed in a mixed halide solution or dispersion characterized in that the apparatus further comprises means for applying an electrical pulse to the silver electrode so that, when the apparatus is in use, a first phase of the pulse electrochemically strips the silver electrode surface and a second phase of the pulse electrochemically coats the electrode with a silver halide consistent with the halide ion ratio of the solution or dispersion and wherein said means for applying the electrical pulse provides a constant controlled voltage versus a reference electrode and wherein means are provided whereby the difference of the voltage is determined by a calculation based on a previous measurement cycle.

9. Apparatus according to claim 8 wherein the means for applying an electrical pulse to the silver electrode comprises a counter electrode and means for generating an alternating current between the silver electrode and the counter electrode.

10. Apparatus according to claim 9 further comprising switching means for alternately connecting and disconnecting the means for applying an electrical pulse and the means for measuring the potential difference.

11. Apparatus according to claim 3 further comprising timing means for controlling duration of the pulse, the duration of measurement of potential difference and any delay therebetween, and control means for controlling size of the pulse.

12. Apparatus according to claim 8 comprising a plurality of silver electrodes and means for applying an electrical pulse to the silver electrodes so that, when the apparatus is in use, the steps of applying the pulse to each electrode and measuring the potential difference overlap without coinciding.

13. A method of measuring the silver ion activity of a mixed halide solution or dispersion which comprises measuring potential difference between a silver electrode and a reference electrode immersed in the solution or dispersion characterized in that prior to measuring the potential difference an electrical pulse is applied to said silver electrode which in a first phase electrochemically strips the surface of said electrode and in a second phase electrochemically coats the surface of said electrode with a silver halide consistent with the halide ion ratio of the solution or dispersion and wherein said means for applying the electrical pulse provides a constant controlled voltage versus a reference electrode and wherein means are provided whereby the difference of the voltage is determined by a calculation based on a previous measurement cycle.

14. A method according to claim 13 wherein the electrical pulse provides a current of from 0.01 mA to 10 mA.

15. A method according to claim 13 wherein the electrical pulse is a square wave pulse.

16. A method according to claim 13 wherein the surface of the silver electrode has an area of from 1 $mm^2$ to 600 $mm^2$.

17. A method according to claim 13 wherein the application of the pulse is followed by a period of delay before measurement occurs.

18. A method according to claim 13 wherein the cycle of events represented by the application of the pulse, the second phase and the measuring is repeated a number of times.

19. A method according to claim 13 wherein the cycle of events takes from 10 msecs to 1 sec.

20. A method according to claim 13 wherein the pulse is from 2 msecs to 100 msecs.

21. Apparatus for measuring the silver ion activity of a mixed halide solution or dispersion which comprises a silver halide coated silver electrode, a reference electrode and means for measuring the potential difference between the electrodes when they are immersed in a mixed halide solution or dispersion characterized in that the apparatus further comprises means for applying an electrical pulse to the silver electrode so that, when the apparatus is in use, a first phase of the pulse electrochemically strips the silver electrode surface and a second phase of the pulse electrochemically coats the electrode with a silver halide consistent with the halide ion ratio of the solution or dispersion and wherein said means for applying the electrical pulse provides a constant controlled current and wherein means are provided whereby the difference of the current is determined by a calculation based on a previous measurement cycle.

22. Apparatus according to claim 21 further comprising timing means for controlling duration of the pulse, duration of measurement of potential difference and any delay therebetween, and control means for controlling size of the pulse.

23. Apparatus according to claim 21 comprising a plurality of silver halide coated silver electrodes and means for applying an electrical pulse to the silver electrodes so that, when the apparatus is in use, the steps of applying the pulse to each electrode and measuring the potential difference overlap without coinciding.

* * * * *